United States Patent
Sioshansi et al.

(10) Patent No.: US 6,293,899 B1
(45) Date of Patent: *Sep. 25, 2001

(54) TRANSMUTABLE RADIOTHERAPY DEVICE

(75) Inventors: Piran Sioshansi, Lincoln; Raymond J. Bricault, West Boylston, both of MA (US)

(73) Assignee: RadioMed Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/187,659

(22) Filed: Nov. 6, 1998

Related U.S. Application Data

(63) Continuation-in-part of application No. 09/046,744, filed on Mar. 24, 1998.

(51) Int. Cl.$^7$ ................................................. A61N 5/00
(52) U.S. Cl. ................................................................. 600/3
(58) Field of Search ................................................ 600/1–8

(56) References Cited

U.S. PATENT DOCUMENTS

| | | | |
|---|---|---|---|
| 4,702,228 | 10/1987 | Russell, Jr. et al. | |
| 4,754,745 | 7/1988 | Horowitz. | |
| 4,946,435 | 8/1990 | Suthanthiran et al. | 600/3 |
| 5,030,195 | 7/1991 | Nardi | 600/7 |
| 5,059,166 | 10/1991 | Fischell et al. | 600/3 |
| 5,342,283 | 8/1994 | Good | 600/8 |
| 5,395,300 | 3/1995 | Liprie | 600/3 |
| 5,405,309 | 4/1995 | Carden, Jr. | 600/3 |
| 5,498,227 | * 3/1996 | Mawad | 600/3 |
| 5,503,614 | 4/1996 | Liprie | 600/7 |
| 5,514,071 | 5/1996 | Sielaff, Jr. et al. | 600/3 |
| 5,575,749 | 11/1996 | Liprie | 600/3 |
| 5,624,372 | 4/1997 | Liprie | 600/3 |
| 5,637,073 | 6/1997 | Freire | 600/3 |
| 5,713,828 | 2/1998 | Coniglione | 600/7 |
| 5,840,009 | 11/1998 | Fischell et al. | 600/3 |
| 5,897,573 | 4/1999 | Rosenthal et al. | 606/224 |
| 5,906,573 | 5/1999 | Aretz | 600/3 |
| 5,976,106 | * 11/1999 | Verin et al. | 604/96 |
| 6,024,690 | * 2/2000 | Lee et al. | 600/3 |
| 6,030,333 | * 2/2000 | Sioshansi et al. | 600/3 |

OTHER PUBLICATIONS

International Search Report for PCT/US00/08948, Jul. 13, 2000.
Jul. 1999 Copy of International Search Report in corresponding International Application No. PCT/US99/02692.
Eigler et al., "A$^{48}$ Vanadium Brachytherapy Source for Treatment of Coronary Artery Restenosis", *Vascular Brachytherapy*, Chapter 23, pp. 231–236, 1996.

* cited by examiner

*Primary Examiner*—Samuel G. Gilbert
(74) *Attorney, Agent, or Firm*—McDermott, Will & Emery

(57) ABSTRACT

A general purpose radiotherapy device can be fabricated to net or near-net shape and then made radioactive in a single activation step. The device is made at least partially of a transmutable material which is transformable to a radioisotope-containing material upon activation by an accelerated beam of charged particles, such as protons, deuterons or alpha particles. The transmutable material is preferably rhodium and the radioisotope preferably comprises palladium-103. The beam energy and device dimensions are selected so that energy from the beam in the range which is most likely to produce a desired transmutation reaction in the device is absorbed, while at least a portion of the energy which is insufficient to effect the desired transmutation reaction is not retained in the device.

5 Claims, 11 Drawing Sheets

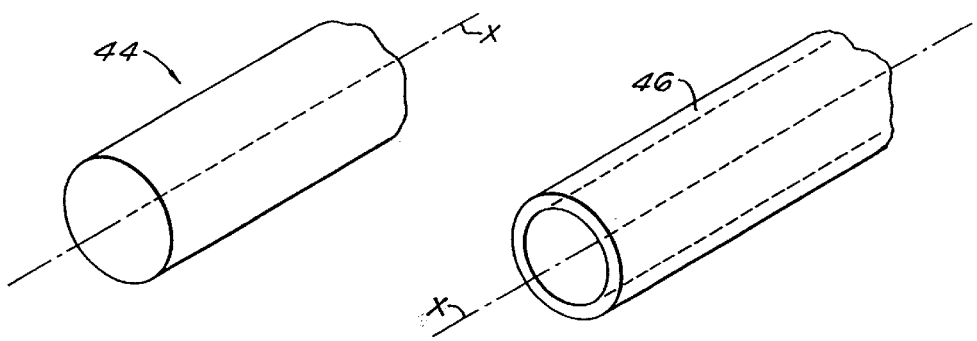
*FIG. 4*  *FIG. 5*
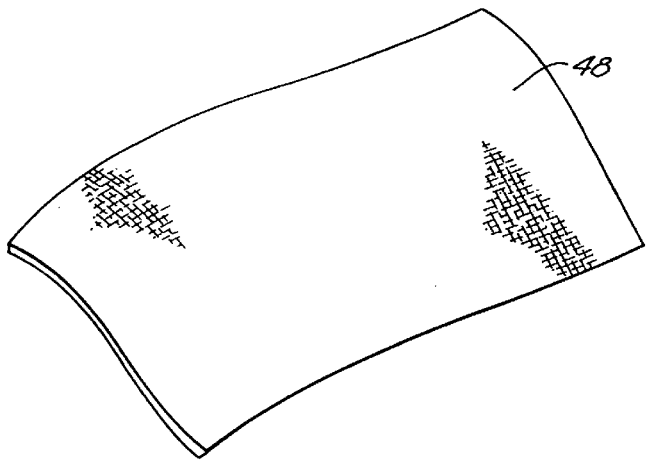
*FIG. 6A*
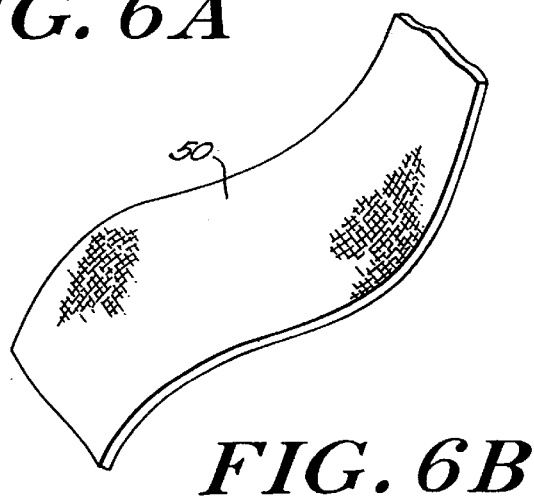
*FIG. 6B*

TRANSMUTABLE RADIOTHERAPY DEVICE

CROSS-REFERENCE TO RELATED APPLICATIONS

This application is a continuation-in-part of copending U.S. application Ser. No. 09/046,744, filed on Mar. 24, 1998, and assigned to the assignee of the present invention.

TECHNICAL FIELD

The invention is directed to implantable radiotherapy devices which can be made radioactive after being formed to a desired final or near-final shape.

BACKGROUND OF THE INVENTION

Tumors, stenoses of biological conduits, and other proliferative tissue can be effectively treated with radiation, which is known to inhibit cellular proliferation. The mechanism by which radiation prevents such proliferative cellular response is by preventing replication and migration of cells and by inducing programmed cell death (apoptosis).

Cells are variably susceptible to radiation, dependent on the types of cells and their proliferative status. Rapidly proliferating cells are generally more radiation-sensitive, whereas quiescent cells are more radiation-tolerant. High doses of radiation can kill all functions of even quiescent cells. Lower levels can merely lead to division delays, but the desirable effect of reproductive death is still obtained. In this case, the cell remains structurally intact but has lost its ability to proliferate, or divide indefinitely.

Traditional high-dose external beam radiation treatment, and prolonged low dose rate, close-distance radiation treatment (brachytherapy), are well-established therapies for the treatment of cancer, a malignant form of cellular proliferation. In particular, attention is currently being directed to the practical aspects of the use of brachytherapy. These aspects are, of course, particularly significant when radioactivity is involved. A disease site in a patient may be exposed to radiation from an external beam, either as a stand-alone procedure or in conjunction with an operative procedure. Alternatively, the radioactivity may be incorporated into an implantable device. In the first case, a higher energy radiation source is used to achieve the necessary penetration of radiation into the tissue to be treated. As a result, other organs or tissue may be unnecessarily exposed to radiation, and safety, handling and logistics problems arise. In the second case, the implantable devices may be quite expensive. In particular, if radioactivity is added to the device, the device may only be effective for radiotherapy during a relatively short period during which the radioactivity is provided at a useful (therapeutic) level. Depending on the radioisotope used, the decay time may be as short as hours, days or weeks.

The current state of the art brachytherapy for treatment of localized lesions such as tumors of, for example, the prostate, breast, brain, eye, liver, or spleen, employs radioactive, "sealed source" seeds. The term "sealed source", as used herein, means that radioisotopes incorporated into a device are integral with the device and cannot be dislodged or released from the host material of the device in the environment of usage. A typical sealed source seed includes a radiation source encapsulated within an impermeable, biocompatible capsule made of, for example, titanium, which is designed to prevent any leaching or release of the radioisotope. The seeds are approximately the size of a grain of rice (typically 0.81 mm in diameter by 4.5 mm long) and are implanted individually at a treatment site within and/or around a lesion, typically with a medium bore (18-gauge) delivery needle.

Disadvantages of the use of such seeds as radiotherapy devices include their nature as discrete, or point, sources of radiation, and the corresponding discrete nature of the dosages which they provide. In order to provide an effective radiation dose over an elongated or wide target area, the seeds should be uniformly and relatively closely spaced. The need to ensure accurate and precise placement of numerous individual radiation sources undesirably prolongs the surgical procedure, and hence the exposure of the surgical team to radiation. Moreover, the use of discrete seeds requires an elaborate grid matrix for their proper placement. This requirement is labor-intensive, and therefore costly. In addition, the discrete nature of the seeds renders them more susceptible to migration from their intended locations, thereby subjecting portions of the lesion, the treatment site, and surrounding healthy tissue to over- or under-dosage, reducing the effectiveness and reliability of the therapy.

Other disadvantages exist in radioactive seed therapy. Relatively few radionuclides are suitable for use in sealed-source seeds, because of limited availability of radioisotopes with the necessary combination of half-life, specific activity, penetration depth and activity, and geometry. In addition, the implantation of seeds generally requires a delivery needle with a sufficiently large bore to accommodate the seeds and may, in some cases, require an additional tubular delivery device. The use of a relatively large delivery needle during seeding may cause unnecessary trauma to the patient and displacement of the lesion during the procedure. Also, because of the risk of migration or dislodgement of the seeds, there is the risk that healthy tissues near or remote from the lesion site will be exposed to radiation from seeds which have become dislodged from their intended locations and possibly carried from the body within urine or other fluids. In addition, radioactive seed therapy is inadequate for treating certain types of intraluminal tissue proliferation, such as, for example, stenosed coronary arteries, and therefore a need exists for more suitable radiotherapy devices for such intraluminal brachytherapy applications.

Radiotherapy devices made of palladium-103 are desirable because palladium-103 has a half life of about 17 days and a photon energy of 20.1–23 KeV, which makes it particularly suitable for use in the treatment of localized lesions of the breast, prostate, liver, spleen, lung and other organs and tissues. Because palladium-103 is unstable and not naturally occurring in the environment, it must be manufactured, generally either by neutron activation of a palladium-102 target, or by proton activation of a rhodium target. In the neutron activation process, a palladium-102 isotope is exposed to a neutron flux in a nuclear reactor to convert palladium-102 to palladium-103. The extent of the conversion is dependent on the neutron flux and the duration of the bombardment in the reactor. The palladium-103 thus formed is fabricated into radioactive seeds. This approach is disclosed in, for example, U.S. Pat. No. 4,702,228 to Russell, Jr. et al.

The neutron activation approach for the transmutation of Pd-102 to Pd-103 can be prohibitively expensive, as the natural abundance of palladium-102 is less than one percent. Enrichment of this isotope to even 20% levels is very costly. In addition, the utility of this process is unsatisfactory, as other isotopes of palladium and other elements, as well as impurities, may be formed and/or activated in the process and can alter or otherwise interfere with the desired radiation, unless further purification is performed.

In the proton activation process, a rhodium-103 target is provided which is irradiated with a proton beam to transform a portion of the rhodium to palladium-103. This process requires that the rhodium-103 target be cooled and then irradiated until a sufficient amount of palladium-103 is obtained to enable chemical separation of the palladium from the rhodium. The rhodium target is then immersed in a strong solvent to separate palladium-103 from rhodium-103. The palladium-103 radionuclides can now be used directly or formed into compounds for later use. This material is generally absorbed into or otherwise incorporated into a non-radioactive carrier material which is then placed into a non-radioactive secondary container, such as a titanium can or shell, and sealed to form a radioactive seed. The secondary container may include some type of radiopaque marker to allow it to be radiographically visible. This approach is disclosed in, for example, U.S. Pat. No. 5,405,309 to Carden, Jr.

The proton activation approach also has disadvantages. The process requires wet chemistry separation to isolate palladium-103 from rhodium-103, and this and other necessary steps have associated yield losses. The disadvantages of discrete seeds in brachytherapy applications have already been discussed.

U.S. Pat. No. 5,342,283 to Good discloses multi-layer radioactive microspheres and wires which are made by forming concentric radioactive and other coatings on a substrate. The radioactive coatings are made by various deposition processes, including ion plating and sputter deposition processes, as well as via exposure of an isotope precursor, such as palladium-102, to neutron flux in a nuclear reactor. The radioactive wires may have nonuniform distributions of radioactivity over their surfaces, as needed for a particular treatment.

A disadvantage of the Good radioactive devices is that they cannot be made economically or simply. As previously mentioned in connection with the creation of palladium-103 from palladium-102 using neutron flux, such processes are prohibitively expensive and require lengthy and costly wet chemistry separation steps to isolate the radioactive isotope from the non-radioactive precursor. Further, the coating methods disclosed by Good for making radioactive coatings are relatively complicated, multistep processes which are difficult to control. In addition, the multiple coatings of the Good devices may detach, deteriorate, flake, spall, peel, leach or otherwise degrade with time and/or exposure to bodily fluids, resulting in dissemination of radioactive and other materials into the body, with potentially harmful consequences.

A relatively recent article by Eigler et al. (circa 1996) discloses methods of proton activation of a nickel-titanium stent for use in intracoronary brachytherapy applications to produce a vanadium-48 radioisotope on the surface of the stent via transmutation. This approach at least eliminates the cumbersome wet chemistry processes of the prior art proton activation processes; however, it too has its deficiencies.

It would therefore be an advancement in the art to provide a general purpose radiotherapy device which can be relatively easily and economically fabricated.

OBJECTS OF THE INVENTION

An object of the present invention is to provide a general purpose radiotherapy device which can be used to deliver a wide variety of radiation treatments.

Another object of the present invention is to provide a general purpose radiotherapy device which obviates the disadvantages of the prior art radiotherapy seeds and similar devices.

Another object of the present invention is to provide a general purpose radiotherapy device which can be fabricated to a desired net or near-net size and shape, and all or a portion of the device rendered radioactive in a relatively simple one-step activation process, without lengthy chemical separation steps.

And another object of the present invention is to provide a general purpose radiotherapy device made of a transmutable material which can be made radioactive upon exposure to an accelerated beam of charged particles.

Still another object of the invention is to provide a general purpose radiotherapy device which is made of a material which can be fabricated to net or near-net shape while in a non-radioactive state, and then made radioactive, and further formed or finished, if and as needed, in a radioactive state.

Another object of the invention is to provide a general purpose radiotherapy device which can be either temporarily or permanently implanted in a patient to deliver radiation in situ.

Still another object of the invention is to provide a general purpose radiotherapy device which provides radiation in a dose and distribution pattern that can be tailored or customized to any particular therapy requirement during fabrication and activation of the device.

Another object of the invention is to provide a general purpose radiotherapy device which emits radiation in a pattern that can vary over the length or breadth of the device and is not dependent solely on the shape of the device.

Another object of the invention is to provide a radioactive surgical fastening device, such as, for example, a staple, suture, pin, plate, screw, nail, or the like, which is made at least partially of a transmutable material which can be made radioactive in a single activation step.

SUMMARY OF THE INVENTION

The radiotherapy device of the present invention provides an effective alternative to traditional encapsulated radioactive seeds or sandwiched structures. The nature of the radiotherapy device disclosed herein allows it to be fabricated to virtually any desired net or near-net size and shape while it is in a non-radioactive state, and then all or a portion of the device rendered radioactive. The device can then be implanted into a patient either temporarily or permanently. Alternatively, the device can be formed to an intermediate or near-net shape while in a non-radioactive state, and then all or a portion of the device made radioactive, and then formed as needed to a final shape while in a radioactive state. During fabrication of the device, input heat from a proton beam is minimized while heat dissipation is maximized, and the device is dimensioned so that optimum transmutation yields can be achieved within a desired range of proton beam activation energies.

The use of accelerated beam technology to make all or a portion of the device radioactive lowers the unit cost of the device, allows greater flexibility in the design and use of the device, eliminates the need for laborious wet chemistry separation procedures, and provides solutions to the problems of heat management and transmutation efficiency during fabrication of the device. The device can be made to net or near-net shape in a variety of geometries, and all or any portion of the device can be made radioactive, so that it can be used in a wide variety of applications. Other advantages will be detailed more fully below.

According to another aspect of the invention, there is provided a method of delivering radiation in situ to a treatment site in a patient. The method comprises the steps of:

a. Providing a radiotherapy device which is at least partially made of a transmutable material which is transformable to a radioisotope-containing material upon activation by an accelerated beam of charged particles, the transmutable portion being formed to at least near-net shape;

b. Activating at least the transmutable portion of the device with a beam of charged particles at sufficient energy to form the radioisotope-containing material; and c. Placing the device at the treatment site in the patient so that the treatment site is exposed to the radioisotope-containing material.

The method can include the further step of forming the transmutable portion of the device to a desired net shape prior to activation, or to a desired near-net shape prior to activation and to a desired net shape after activation. In addition, the method can include the step of activating the transmutable portion of the device so that the device emits radiation in a pattern having a shape which is determined at least in part by the distribution of radioisotope-containing material within the transmutable portion of the device and not solely by the shape of the device. This distribution can be either substantially constant or variable. The method can include the further step of applying a substantially radiation-transparent encapsulating material to at least a portion of the surface of the device. In addition, or alternatively, the method can include the step of applying a substantially radiation-transparent, non-radioactive agent to at least a portion of the surface of the device. A radiopaque marker can also be incorporated into the device.

According to still another embodiment of the invention, a kit for delivering in situ a predetermined dose of radiation to a treatment site in a patient comprises a general purpose radiotherapy device, as described above, and a delivery vehicle for placing the device into the patient. In a preferred embodiment, the device is in the form of an elongated element and the delivery vehicle is a biopsy needle fitted with an injector device.

According to another aspect of the invention, there is provided a net or near net shape implantable radiotherapy device, comprising a net or near net radiotherapy delivery structure made substantially of a transmutable material. A portion of the transmutable material is transformed into a radioisotope-containing material upon activation by a beam of charged particles having energy above a predetermined threshold energy. At least a portion of the energy in excess of the predetermined threshold energy is captured within the radiotherapy delivery structure and used to form the radioisotope-containing material, while at least a portion of the energy below the threshold energy (principally manifested as heat) is not retained in the structure.

In a preferred embodiment, the transmutable material comprises rhodium and the radioisotope comprises palladium-103. The beam of charged particles preferably comprises protons which have an energy of at least approximately 4 MeV. The predetermined threshold energy of the charged particles is at least approximately 6 MeV.

The transmutable portion of the device is formable either to a desired net shape prior to activation, or to a desired near-net shape prior to activation and to a desired net shape after activation, i.e., while in a radioactive state.

The device preferably emits radiation in a pattern having a shape which is determined at least in part by the distribution of the radioisotope-containing material within the transmutable portion of the device and not solely by the shape of the device. In one embodiment, the distribution of radioisotope-containing material is substantially constant; in another embodiment, it is variable.

The radiotherapy delivery structure can be any two- or three-dimensional shape, such as, for example, a wire, a stent, a planar or contoured plaque, or a tip for a wire, such as a guidewire. The structures can be layered, stacked, coiled or otherwise formed to increase the effective thickness of the device in the direction of beam penetration.

In one embodiment, the device is in the form of an elongated element which can be substantially solid or tubular. The elongated element preferably has an aspect ratio of at least 3 to 1. In one preferred embodiment, the elongated element is in the form of a wire. The wire can include a transmutable portion at one or both ends thereof or at any intermediate portion. The elongated element can be formed into any two-dimensional or three-dimensional shape, such as a zig-zag or helix.

In another embodiment, the device is in the form of a two-dimensional sheet or a three-dimensional shape. In one preferred embodiment, the device is in the form of a spherically contoured plaque having a concave surface and a convex surface. At least a portion of the concave surface is activatable and includes palladium-103.

In still another embodiment, the device is in the form of a seed.

A portion of the device may include a non-transmutable material which is preferably selected from the group consisting of non-transmutable metals, nonmetals, polymers and composite materials.

The device can further include a substantially radiation-transparent encapsulating material which is applied to at least a portion of the surface of the device. Alternatively, or additionally, the device can include a substantially radiation-transparent, non-radioactive agent applied to at least a portion of the surface of the device. The non-radioactive agent is preferably selected from the group consisting of therapeutic agents and lubricating agents.

The device can further include a radiopaque marker to make it visible under x-rays.

In one embodiment, the device is adapted for surgical fastening of tissue at a wound repair site and is preferably a device such as, for example, a staple, suture, clip, pin, nail, screw, plate, barb, anchor or a patch.

The device can be adapted for either temporary or permanent placement within the patient and may include one or more anchors suitable for such purpose.

The transmutation of the radiotherapy delivery structure, and the heat production within the structure, are each a function of the initial energy of the beam entering the structure and the thickness of the structure in the direction of beam penetration.

According to another aspect of the invention, there is provided a method of making a net or near net shape radiotherapy device. The method comprises the steps of:

a. Providing a net or near net shape radiotherapy delivery structure made substantially of a transmutable material; and b. Activating the transmutable material of the radiotherapy delivery structure with a beam of charged particles having energy above a predetermined threshold energy to transform a portion of the transmutable material into a radioisotope-containing material. At least a portion of the energy in excess of the predetermined threshold energy is captured within the radiotherapy delivery structure and used to form the radioisotope-containing material, while at least a portion of the energy below the threshold is not retained in the structure.

In a preferred embodiment, the method can include the further step of scanning the beam of charged particles across the surface of one or more radiotherapy delivery structures to reduce the average power density on them. Alternatively, the method can include the further step of moving the radiotherapy delivery structure or structures through the beam. The beam may also be enlarged to cover a relatively large area on the surface of the radiotherapy delivery structure so as to minimize local power density thereon. For example, the beam can be directed toward the radiotherapy delivery structure from a preselected distance so as expand the beam coverage area over a substantial portion of the surface of the radiotherapy delivery structure. Alternatively, the beam can be directed through a beam-expanding element prior to impingement on the radiotherapy delivery structure.

In a preferred embodiment, the beam of charged particles is provided by a linear accelerator or a cyclotron.

The method can further include the step of cooling the radiotherapy delivery structure by placing it in thermal communication with a medium for effecting heat transfer from the structure. For example, the radiotherapy delivery structure may be in contact with a heat transfer medium, such as a gas, or a substantially non-activatable and thermally conductive heat dissipating member. Alternately, the radiotherapy delivery structure may be atmospherically isolated from the the source of the high-energy beam, which is generally maintained at a high vacuum, so that enhanced convective and/or conductive cooling is possible. Radiative cooling is also an effective mechanism for heat transfer from the radiotherapy delivery structure in a vacuum environment.

In various preferred embodiments of the invention, the radiotherapy device can be, for example, a stent, a microwire, a tip for a wire, a plaque, or any other suitable structure for providing radiation therapy at a particular treatment site.

BRIEF DESCRIPTION OF THE DRAWINGS

The foregoing and other features and advantages of this invention will be better understood from the following detailed description taken with the accompanying drawings, in which:

FIG. 4 is a perspective view of a device in the form of a solid wire according to one embodiment of the invention;

FIG. 5 is a perspective view of a device in the form of a tube according to another embodiment of the invention;

FIG. 6A is a perspective view of a device in the form of a substantially two-dimensional flat sheet according to another embodiment of the invention;

FIG. 6B is a perspective view of a device in the form of a substantially three-dimensional shape according to another embodiment of the invention;

Like features in the FIGURES are indicated by like reference numbers.

DETAILED DESCRIPTION OF THE DRAWINGS

Figure 1:
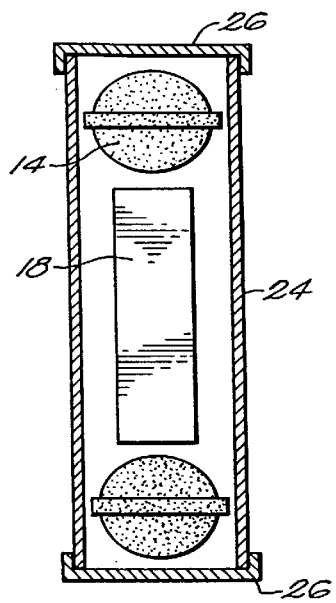
FIG. 1 is a cutaway view of a prior art radioactive seed made by exposing a non-radioactive palladium-102 target to neutron flux to obtain radioactive palladium-103, as known in the art.

The invention is directed to radiotherapy devices which can be fabricated from a substantially non-radioactive material and then transformed, via exposure to a high-energy beam of charged particles, into a radioactive material. The device can be manufactured to net shape before it is made radioactive, and therefore it can be easily and economically worked, handled, transported and stored in a non-radioactive state. Alternatively, a device which is already radioactive can be shaped to a final net shape just prior to use in order to customize a particular treatment. Significant advantages of the device of the present invention include the relative ease and economy with which it can be fabricated, the ability to fabricate the device either before or after radioactivation, and the ability to customize the device for a wide variety of radiotherapy applications as a result of the simplified fabrication and radioactivation process.

The term "implantable", as used herein, means any device which can be surgically introduced into or onto a patient for either temporary or permanent placement. The term "transmutable" refers to the ability of a non-radioactive material to be converted, through nuclear transformation, into a radioactive material upon exposure to an accelerated beam of charged particles. The terms "net shape" and "near-net shape", as used herein, refer, respectively, to a final or near-final size and/or shape of the device and not any particular geometric shape, but do not preclude additional, relatively minor formation steps, such as, for example, wire forming or cutting, sheet bending or cutting, punching, piercing, stamping, drawing, extruding, flattening, grinding, and the like, as well as surface treatments such as, for example, polishing, peening, knurling, scoring, abrading, and the like. The term "radioactivation", as used herein, refers to the process by which a transmutable, non-radioactive material is made radioactive upon exposure to an accelerated beam of charged particles, such as protons, deuterons, or alpha particles, at an energy of greater than about 4 MeV.

The term "sealed source equivalent", as used herein, refers to a radioactive device which bears the characteristics of a "sealed source", i.e., in which the radioactive portion of the device is an integral part of the device that cannot otherwise be dislodged, released or separated from the device in the environment of usage.

The device is preferably made at least partially of a transmutable material which can be transformed into a radioisotope-containing material upon activation by an accelerated beam of charged particles. The transmutation process is preferably effected in a nuclear accelerator or cyclotron and is highly efficient if a beam of sufficiently high-energy particles is used.

The transmutable portion of the device is preferably formed to at least near-net shape and in a preferred embodiment is made of rhodium, which is transmutable in part to radioactive palladium-103 upon exposure to an accelerated beam containing protons, deuterons or alpha particles.

The device can be fabricated to virtually any desired size and shape for the intended treatment application. For example, if an elongated wire is needed to provide a linear radiation source, a solid rhodium ingot can be drawn to the desired final dimensions of the filament. All or a portion of the wire can then be radioactivated upon exposure to an accelerated charged particle beam, effecting transmutation of the exposed rhodium to radioactive palladium-103. Alternatively, the rhodium ingot can be drawn to a desired intermediate size and/or shape, radioactivated in that intermediate state, and further shaped, formed or cut to the desired final dimensions just prior to implantation of the device in the patient.

Other geometries which may be useful for certain radiotherapy treatments include, for example, tubular structures, such as stents, substantially flat thin sheets or foils which may be contoured around the whole or a part of an organ or other structure, and even discrete seeds, which can be conveniently formed by activating elongated rhodium wires at an appropriate energy level to obtain palladium-103 wires, and then cutting the wires to the desired dimensions. Alternatively, the rhodium wires can be cut to the desired dimensions prior to activation and transmutation to palladium-103.

The device can be made entirely of a transmutable material, such as rhodium-103, or it may be made partially of a substantially non-transmutable material. The transmutable material can be attached to the nontransmutable material, such as by welding or other joining means, or it may be incorporated into or onto portions of the nontransmutable material, such as by plating, diffusion, ion implantation, or other deposition or penetration techniques. Materials which are suitable for use as the non-transmutable portion of the device can include, for example, substantially non-transmutable metals, nonmetals, polymers, and composite materials.

Alternatively, the device can be made entirely of a transmutable material, with only a portion of the transmutable material being transformed, via irradiation with a beam of particles at a sufficient energy, to a radioactive material. Transmutation of a non-radioactive species to a radioactive species does not effect a total conversion of the non-radioactive species, and thus a portion of the non-radioactive species is present with the radioactive species after transmutation has occurred. The ability to activate only a portion of the device, such as by choosing a device thickness that would not result in complete penetration of the activating beam energy, or setting the activating energy at a level which is not sufficiently high to effect the desired transmutation reaction within or throughout the device, or by selective masking of portions of the device prior to and during activation, and thus attenuating the beam energy to correspond to the beam penetration distance in the device, greatly enhances the customization potential and design flexibility of such devices.

If desired, a substantially radiation-transparent, biocompatible encapsulating material can be applied to at least a portion of the radioactive portion of the device to further encapsulate the radioactive portion of the device. The encapsulating material can be applied to the transmutable material prior to transmutation, or it can be applied to the radioisotope-containing material after transmutation. In addition, or alternatively, one or more substantially radiation-transparent, non-radioactive agents can also be applied to all or a portion of the surface of the device to deliver other benefits to the lesion or treatment site. Such agents can include, for example, therapeutic agents and lubricating agents. These agents can also be applied either before or after transmutation has occurred.

FIG. 1 illustrates a prior art radioactive seed, such as is manufactured by Theragenics Corporation (Norcross, Ga). The radioactive seed comprises a titanium tube 24 containing within it two pellets 14 of radioactive palladium-103. The pellets are separated by a radiopaque lead marker 18. The tube is sealed and capped at the ends with welded caps 26. The seeds are approximately the size of a grain of rice and can be implanted in a patient at a treatment site with, for example, 18-gauge delivery needles. Such seeds can be made, for example, by the methods disclosed in U.S. Pat. No. 4,702,228 to Russell, Jr. et al. and U.S. Pat. No. 5,405,309 to Carden, Jr.

Besides the difficulty of fabrication of discrete radioactive seeds according to methods known in the art, the implantation of discrete seeds in the vicinity of a lesion to provide a suitable radiation dosage to the lesion without damaging surrounding healthy tissue is a tedious and labor-intensive process which cannot be reliably controlled to a satisfactory extent. Dosage control in three dimensions is relatively difficult when discrete seeds are used as the radiation delivery vehicle. The patient may suffer significant and unnecessary trauma, not only as a result of implantation of numerous discrete seeds, but also as a result of potential migration of some of those seeds, with attendant damage to adjoining healthy tissue, during the treatment period.

Figure 2:
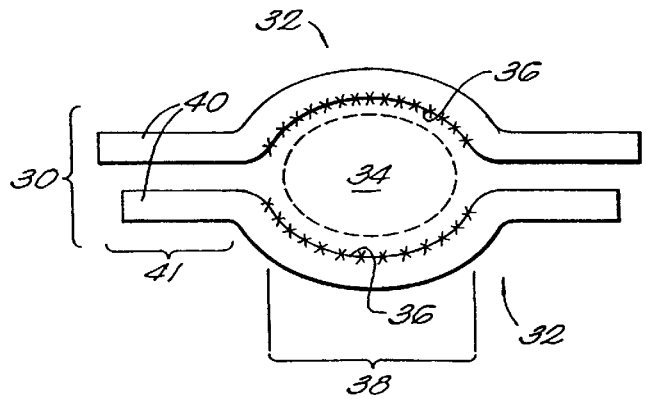
FIG. 2 is a side elevational view of a radiotherapy device according to one aspect of the invention.

FIG. 2 illustrates a typical radiotherapy device 30 fabricated according to the present invention. The device 30 in this embodiment comprises a pair of shaped plates 32 which are made of a substantially non-radioactive transmutable material, such as rhodium. The plates 32 can be fabricated to a desired shape and size for the intended application. Lesion 34 is shown in phantom in FIG. 2 to illustrate a particular application for the device. In this application, the inner surfaces 36 of the central portions 38 of the plates could be activated in a high-energy charged particle beam, while legs 40 extending from either side of the central portions 38 of the plates could be masked during the activation process so as not to be transmutated to a radioactive species. The radioactive portions of the device would emit radiation in a converging pattern toward lesion 34.

Other geometries suitable for delivering a desired radiation dose might include, for example, a thin foil or sheet, or a wire mesh cage or basket, which can be preformed to surround a lesion of a particular size and shape; microfilaments or rods of constant or varying diameter to penetrate or otherwise provide radiation in a linear or radial radiation pattern at a treatment site; or a tubular structure sized to surround a lesion. For example, foils and sheets may be useful in the treatment of substantial areas, such as skin cancers. Such devices can be activated on one side and coated with a radiation-impervious layer on the other side to facilitate delivery of radiation in a single direction only. They can be formed as substantially two-dimensional patches, or they can be further formed before or after activation to complex three-dimensional shapes. Additional formation and contouring of such sheets can further focus or concentrate a pattern of radiation emitted therefrom. Other device geometries suitable for a particular application are considered to be within the scope of the invention.

Figures 3A, 3B, 3C:
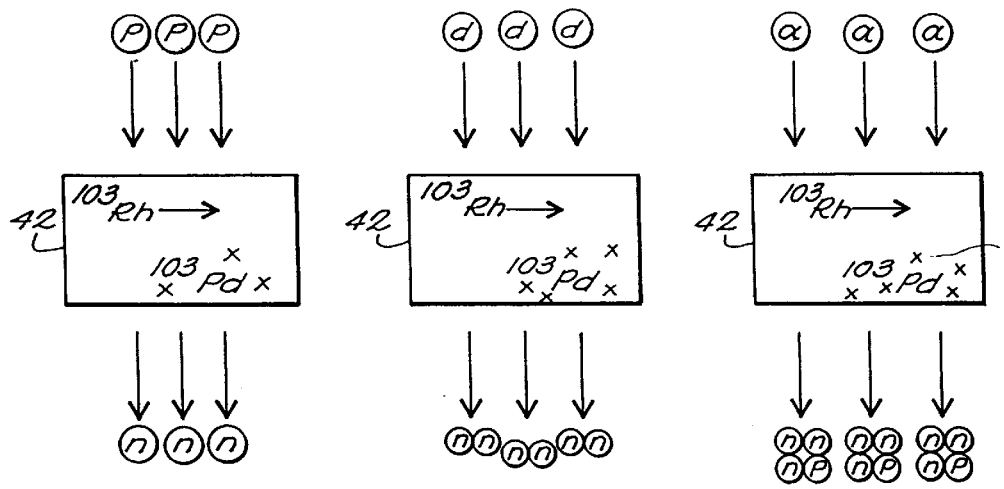
FIG. 3A is a schematic representation of the transmutation of rhodium-103 to radioactive palladium-103 by activation with a proton beam.
FIG. 3B is a schematic representation of the transmutation of rhodium-103 to radioactive palladium-103 with a deuteron beam.
FIG. 3C is a schematic representation of the transmutation of rhodium-103 to radioactive palladium-103 with an alpha particle beam.

FIGS. 3A–3C illustrate three preferred mechanisms for transforming rhodium to radioactive palladium-103. Rhodium and palladium atoms have charge numbers 45 and 46, respectively. Although rhodium exists monoisotopically as rhodium- 03, palladium has several isotopes, one of which is metastable palladium-103.

In FIG. 3A a rhodium target 42 is exposed to a high-energy beam of protons, preferably in the range of approximately 6–18 MeV. The transmutation reaction in the rhodium nucleus involves the capture of a single proton (p) and the emission of a single neutron (n). In FIG. 3B a rhodium target 42 is exposed to a high-energy beam of deuterons (nucleus of deuterium, containing one proton and one neutron). The transmutation reaction involves the capture of a deuteron (d) and the emission of two neutrons (n,n) from the rhodium nucleus to create palladium-103. In FIG. 3C a rhodium target 42 is exposed to a high-energy beam of alpha particles (helium nucleus, containing two protons and two neutrons). The transmutation reaction involves the capture of an alpha particle a and the emission of three neutrons (n,n,n) and one proton (p) from the rhodium nucleus to create palladium-103. In each case, the depth or extent of transmutation depends on the duration of exposure of at least the transmutable portion of the device to the irradiating beam, the energy of the beam, and the thickness of the transmutable material of the device.

FIGS. 4, 5, 6A, 6B and 7 illustrate radiotherapy devices according to various alternative embodiments of the present invention. The device shown in FIG. 4 is in the form of an elongated element 44 which extends along a principal axis X and is preferably in the form of a drawn or extruded wire or rod made of a transmutable material, such as rhodium.

Exposure of the wire 44 to a high-energy beam of charged particles can effect transmutation of a portion of the rhodium to palladium-103. The depth of penetration of a charged particle is a function of the energy of the particle and the thickness of the wire or target in the direction of beam penetration. For example, at a particle energy of about 18 MeV, transmutation depths may be on the order of approximately 500 microns. If the diameter of a wire, or the thickness of a sheet or plaque, is less than approximately 500 microns, transmutation of the entire bulk of the device may occur upon exposure to charged particles at this energy. However, if the device diameter or thickness dimension is greater than approximately 500 microns, transformation will occur to approximately this depth upon activation at this energy, and a core portion of the device at a depth of greater than 500 microns will remain in the form of non-radioactive rhodium. Alternatively, a portion of the device may be masked or otherwise shielded from exposure to the charged particle beam, so that only the unmasked or unshielded (i.e., exposed) portions will be transformed, upon beam exposure, to palladium-103. Thus, the extent of transmutation of a rhodium target is a function of both the energy of the activating beam entering the target, and the thickness of the target in the direction of beam penetration. This understanding permits one to specify either a device geometry or a beam energy, which will then determine the necessary beam energy or device thickness, respectively, for an acceptable degree or extent of transmutation.

The device shown in FIG. 5 is a tube 46 which may be used to surround a lesion or region of tissue to be treated. Irradiation and transmutation of a tube of rhodium would typically be from the outside of the device in toward the central axis X. Other exposure and/or masking schemes may be used to provide a customized transmutation of the material of the device, thereby providing a customized radiation pattern from it.

FIG. 6A illustrates a substantially thin flat sheet or foil 48 which may be fabricated to surround, cover or otherwise closely conform to a lesion to be treated. Thin flat sheets may be particularly advantageous in certain applications, as they can be preformed and easily stored in a non-radioactive state until needed. Once activated, they can be further formed as needed, possibly even in situ, to conform to the contour of the lesion or tissue to be treated.

FIG. 6B illustrates a substantially two-dimensional sheet formed into a substantially three-dimensional complex shape 50, as needed, for example, to conform to an irregularly shaped lesion or treatment area. The sheet may be formed to near-net shape and then radioactivated, or it may be radioactivated and then formed into a final net shape.

Figure 7:
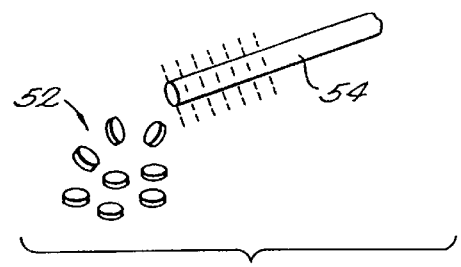
FIG. 7 is a perspective view of a device in the form of a seed according to another embodiment of the invention.

FIG. 7 illustrates a collection of radioactive seeds 52 made according to one aspect of the invention. Unlike the prior art seeds, which are a composite of pellets of radioactive material encased in a non-radioactive titanium shell, the seeds 52 of the present invention can be made directly from rhodium wires 54 which have been radioactivated and then cut to the desired seed dimensions just prior to implantation. Alternatively, the rhodium wires can be cut to desired lengths and the rhodium seeds thus formed stored in a non-radioactive state for later radioactivation. With either method, many costly fabrication steps are avoided in the manufacture of radioactive seeds using the transmutation techniques disclosed herein.

Figure 8:
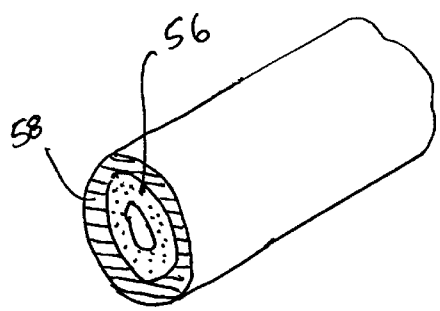
FIG. 8 is a cutaway view of a device in the form of a wire which includes a coating of a radiation-transparent, biocompatible encapsulating material, as well as at least one radiation transparent, non-radioactive agent applied to the surface of the wire.

The radiotherapy device can be further treated with a substantially radiation-transparent, biocompatible encapsulant 56 over at least a portion of its surface, as illustrated in FIG. 8. The purpose of the encapsulant is to provide an additional sealant to prevent leaching of any residual radioactivity from the device after transmutation. The encapsulant coating 56 may be applied to all or a portion of the device, illustrated as a wire 44, either pre- or post-transmutation and may comprise, for example, a polymer, metal, nonmetal, or ceramic. Typical techniques for applying the encapsulant include, for example, plating, sputtering, evaporation deposition, ion plating, plasma spray deposition, flame spray deposition, and chemical vapor deposition. Typical coating thicknesses may range from about 50 Angstroms to about 250 micrometers.

It may be also desirable to apply one or more substantially radiation-transparent, non-radioactive agents 58 over at least a portion of the surface of the device in order to deliver a non-radioactive treatment with the radiation. Such agents can include, for example, therapeutic agents, chemical agents, thermal agents, biological agents such as proteins and growth factors, lubricants or other friction-reduction agents, and other agents useful in various therapies. These agents can be applied either directly onto the transmutable material of the device, to the nontransmutable material of the device if such a substrate material forms part of the device, or onto the encapsulant coating 56. Such agents may be applied, for example, by such processes as immersion of the device in the desired medium, chemical grafting, plasma coating, plasma assisted coating, plasma decomposition coating, vacuum coating (such as by evaporation, sputtering, ion implantation, and ion beam sputtering), plating, chemical vapor deposition, chemical reaction bonding, suspension drying, and the like.

Either or both types of coatings can be applied to the device, or respective portions of the device, as needed.

Figure 9A:
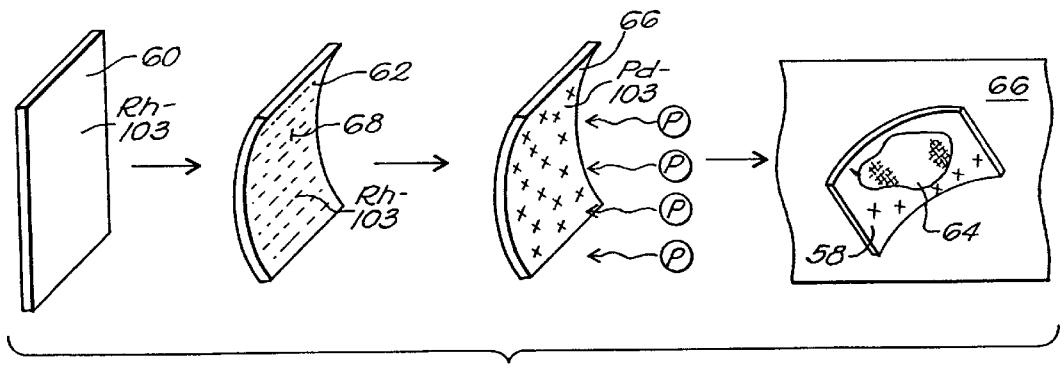
FIG. 9A is a flow diagram illustrating a method of delivering radiation to a localized lesion using a radiotherapy device fabricated according to one aspect of the invention.

FIG. 9A illustrates the steps of a method for treating a localized lesion or disease site in a patient using the techniques of the present invention. A rhodium sheet 60 is provided and formed into a desired shape and size. In this illustration, a flat sheet or foil of rhodium is formed into a contoured patch 62 which is dimensioned to surround or closely conform to a lesion 64 on or within a patient 66. The rhodium sheet 60 is then exposed to an activating beam of charged particles, such as a proton beam, at an energy level of between about 4 and 18 MeV. As illustrated in FIG. 9A, the device may be exposed to the charged particle beam only on one side or in a restricted area, if transmutation of only a portion of the device is desired. In this instance, the concave surface 68 of the sheet is irradiated with protons and transmutated to palladium-103, so that radiation can be emitted from the concave surface toward and into the lesion 64 upon implantation of the device into the patient, with minimal radiation exposure of surrounding healthy tissue.

Figure 9B:
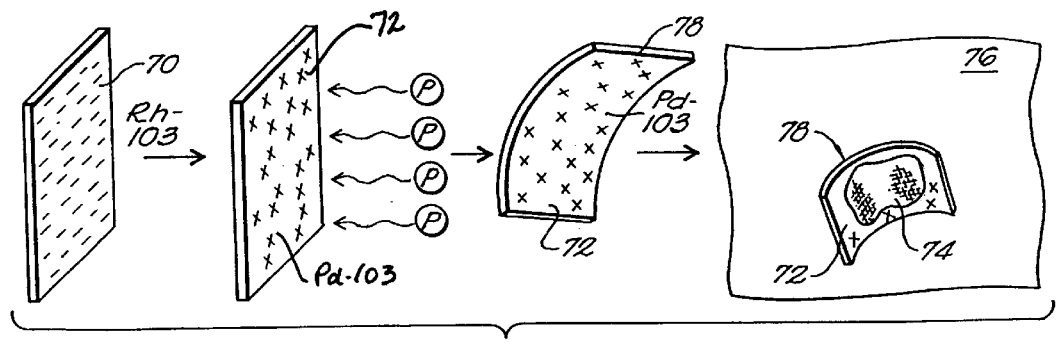
FIG. 9B is a flow diagram illustrating an alternate method of delivering radiation to a localized lesion using a radiotherapy device fabricated according to another aspect of the invention.

FIG. 9B illustrates steps of a method for treating a localized lesion or disease site on or within a patient which requires a radioactive, contoured, three-dimensional shape. In this illustration, a flat sheet made of rhodium 70 is radioactivated in a charged particle beam, preferably by penetration of the charged particle beam into the sheet from one side 72, which will be the side directed to the lesion to be treated 74 in a patient 76 when the sheet is formed into a complex contoured shape 78 while in a radioactive state. The desired net shape and size of the device can be determined from mapping techniques known in the art for mapping the dimensions of lesions within tissue.

If desired, the devices illustrated in FIGS. 9A and 9B can be further treated with a radiation-impervious material on the unactivated side, to minimize radiation emission in a direction away from the region or tissue to be treated.

Figure 10:
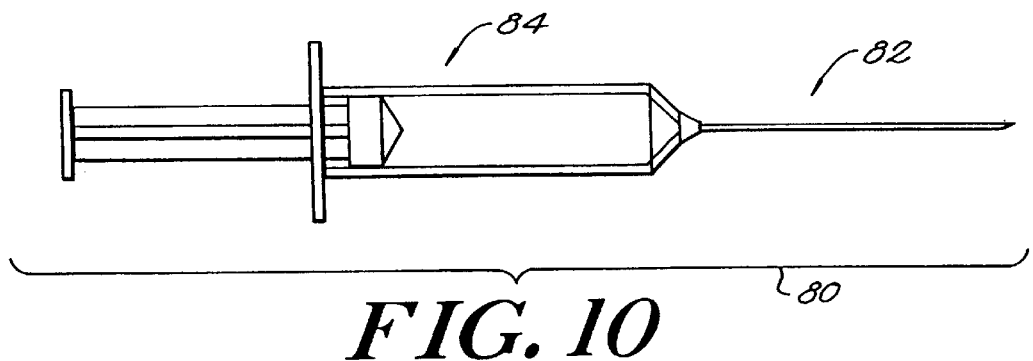
FIG. 10 is a side elevational view of a radiotherapy delivery kit according to another aspect of the invention.

FIG. 10 illustrates a kit for delivering a predetermined dose of radiation to a disease site or lesion within a patient. The kit 80 includes a radiotherapy device in the form of a substantially elongated element 82, such as a wire which can be solid or tubular, as described herein, and a delivery vehicle, such as a syringe 84 or the like, for inserting the elongated element into the patient at or near the treatment site. The radiotherapy device is provided in a form which is suitable for the particular application, such as treatment of prostate tumors. It is made substantially of a transmutable, non-radioactive material, such as rhodium, and can be activated upon exposure to an accelerated charged particle beam to become radioactive.

The use of radioactive wires for the treatment of proliferative tissue is known to be an advancement over the current seeding techniques. The radiation dosage obtainable using radioactive wires can be either substantially uniform or variable over the entire length of the wire. In any event, the dosage can be discriminately applied based upon the specific therapy requirements by tailoring the shape of the device and the radiation pattern emitted from it. In addition, the wires can be positioned accurately and reliably, without migration or dislodgement of the radiation source from its intended position.

The significant advantage of the present invention is the relative ease with which such devices can be manufactured. Near-net shape devices of any desired size and shape can be fabricated and then made radioactive in a single activation step, without the need for elaborate chemical separation processes. Moreover, the ability to fabricate the devices to at least near-net shape before radioactivation provides tremendous design flexibility for the device and provides a means of treating a wide variety of disease sites in a wide variety of locations and stages of development.

Figure 11:
FIG. 11 is a side elevational view of an elongated radiotherapy device having a substantially zig-zag geometry.
Figure 13:
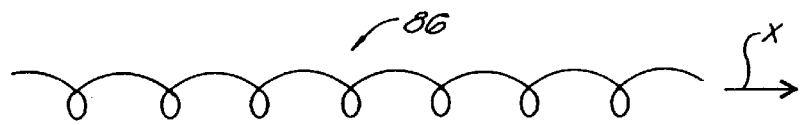
FIG. 13 is a side elevational view of an elongated radiotherapy device having a substantially coiled geometry.
Figure 12:
FIG. 12 is a side elevational view of an elongated radiotherapy device having a substantially serpentine geometry.

The devices can be either substantially solid in cross-section, or tubular, or porous, or of any other geometry which facilitates the administration of a therapeutic dose of radiation to a localized lesion. A wire can be cut to various lengths, either prior to or after high-energy beam radioactivation, to suit the particular application. For example, a preferred length of radioactive wire or filament for use in prostate tumor therapy is between about 10 and 60 mm, and a preferred diameter is between about 0.05 and 0.25 mm. Preferably, the radioactive structure is sized to accommodate a specific treatment region. As illustrated in FIGS. 11 and 12, a wire 86 can be formed, for example, into a two-dimensional zig-zag or serpentine shape, or into a three-dimensional helix or coil, as illustrated in FIG. 13. The device may be rendered radioactive over a portion or the entirety of its length, as needed. It may be formed to near-net shape first, and then radioactivated, or radioactivated first and then formed to its final net shape.

Figure 14:
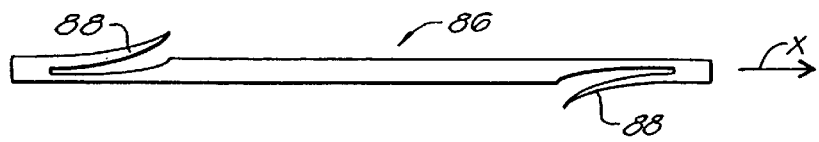
FIG. 14 is a side elevational view of an elongated radiotherapy device having a barbed anchoring element at each end of the device.
Figure 15:
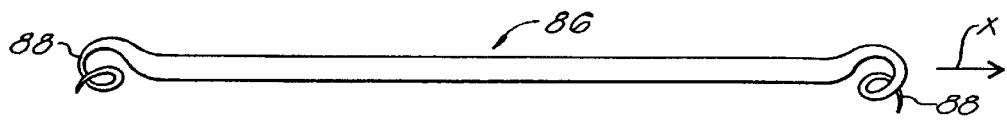
FIG. 15 is a side elevational view of an elongated radiotherapy device having a coiled anchoring element at the each end of the device.

The device can be permanently or temporarily implanted on or in the patient. It can also be removed from the patient after radiotherapy treatment has been completed, undergo reactivation in an irradiating charged particle beam, and reimplanted to deliver radiation in another application. As shown in FIGS. 14 and 15, the device 86 can include a securing element, preferably in the form of one or more anchors or barbs 88 of various forms known in the art, for fixation of the device in the host tissue so that it remains in place after implantation for the duration of the radiation treatment, and possibly indefinitely.

Two applications in which the radiotherapy device of the present invention are of particular interest are the treatment of prostate tumors, both benign and malignant, and the treatment of ophthalmic lesions, such as intraocular melanoma, retinoblastoma, and macular degeneration. Other applications which may also be suitable for treatment with the device of the present invention include the treatment of breast, spleen, liver, lung and brain tumors, as well as other localized tumors.

For example, in the case of radiotherapy of prostate tumors, the radiotherapy device of the present invention may comprise a relatively thin, narrow, elongated member, such as a relatively fine-gauge filament, which can be inserted into or around the tumor. The filament can be substantially solid in cross-section, or it can be tubular. The device can be fabricated into any two-or three-dimensional structure prior to or after radioactivation with a charged particle beam. It can be made fully or partially radioactive, depending on the energy of the beam, the duration of exposure to the beam, the thickness of the device in the direction of beam penetration, and on the existence of any masking or other shielding of any portion of the device. The radiation pattern from such a device thus can generally follow the shape of the device, or it can be tailored to meet specific therapy requirements.

For the treatment of, for example, tumors of the prostate, it is preferred to employ a solid or tubular rhodium wire which is transmutable to palladium-103 upon irradiation with protons, deuterons or alpha particles at an average energy level of at least 4 MeV. Palladium-103 is already used in radioactive seeds used to treat prostate tumors, and thus its behavior in, and suitability for, this application is well-documented. In a preferred embodiment, palladium-103 is incorporated into 20-, 40- and 60 mm wire segments to establish an activity per unit length for each wire which corresponds to the discrete seed activity, or seed source strength, provided by this radioisotope in seed form.

Figure 16A:
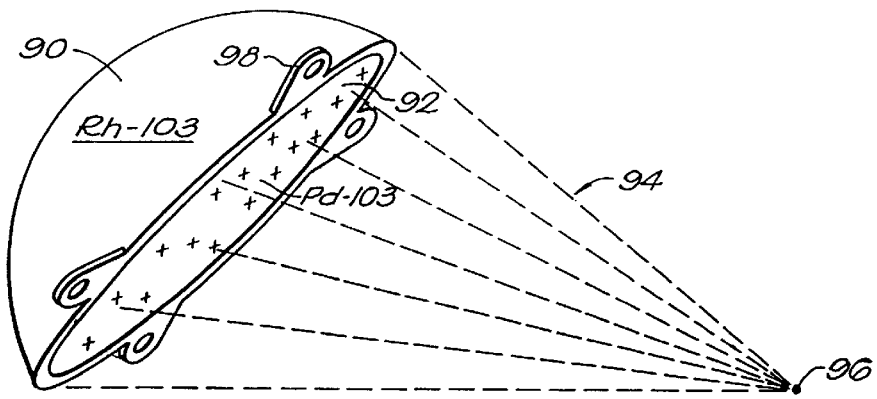
FIG. 16A is a perspective view of a hemispherical plaque useful in the treatment of ocular lesions.
Figure 16B:
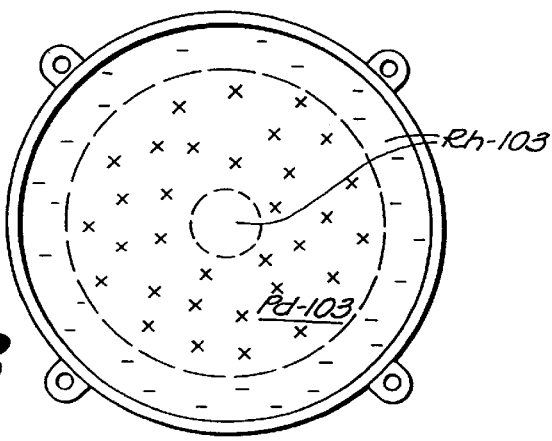
FIG. 16B is an axial view of a hemispherical plaque which has been selectively activated to provide an annular radioactive portion.
Figure 16C:
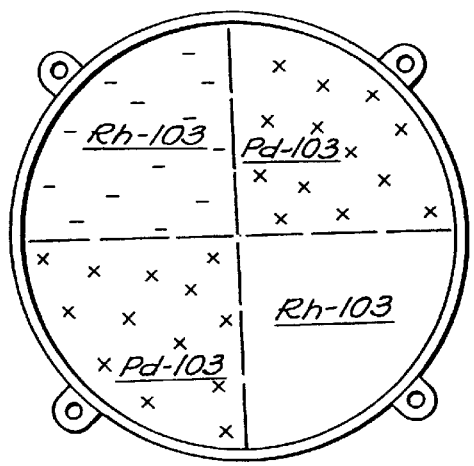
FIG. 16C is an axial view of a hemispherical plaque which has been selectively activated to provide sector-shaped radioactive portions.

In the case of radiotherapy of ophthalmic lesions, the radiotherapy device of the present invention may comprise a hemispherical plaque 90, illustrated in FIGS. 16A–16C, having a substantially spherically contoured shape with a predetermined radius of curvature. Transmutation of the material of the plaque, for example, the concave surface 92 of the plaque, via exposure to a high-energy charged particle beam, will produce a radioactive surface that will define a radiation pattern 94 which converges toward a focal point or region 96 located within the lesion or tissue to be treated. As previously mentioned, selective exposure of the plaque to the accelerated charged particle beam, as well as selective masking of portions of the plaque, can produce, for example, annular or sector-shaped radioactive portions which emit radiation in corresponding patterns, as shown in FIGS. 16B and 16C, respectively. It may be desirable to provide a radiation-impervious coating, such as a layer of gold, on the non-radioactive surface of the device, such as on the convex surface of the plaque, to prevent unwanted irradiation of the skull behind the eye from the radioisotope-containing concave surface of the plaque.

The plaque can include one or more anchors 98 in the form of eyelets or like structures which permit attachment of the plaque to tissue.

Figure 17:
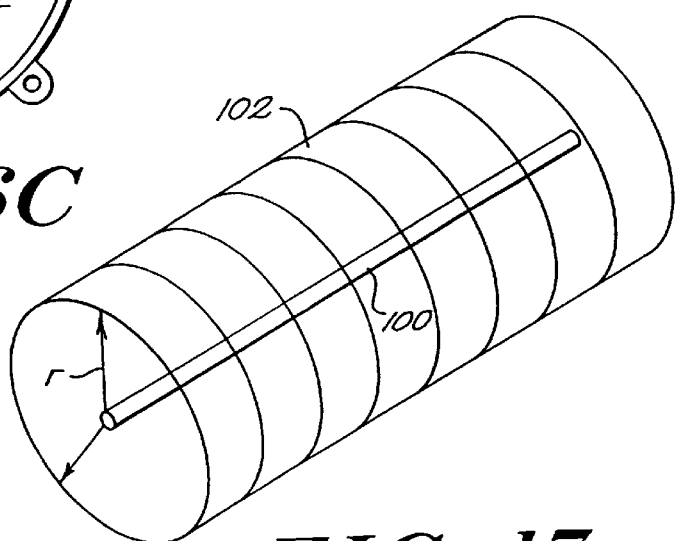
FIG. 17 is a perspective view of an elongated element which has been activated along its length to provide a substantially uniform, constant-radius radiation pattern.
Figure 18:
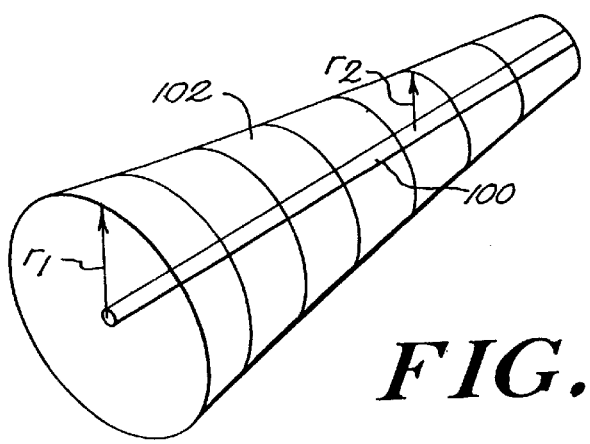
FIGS. 18 and 19 are perspective views of elongated elements which have been activated along their respective lengths to provide varying radiation patterns.
Figure 19:
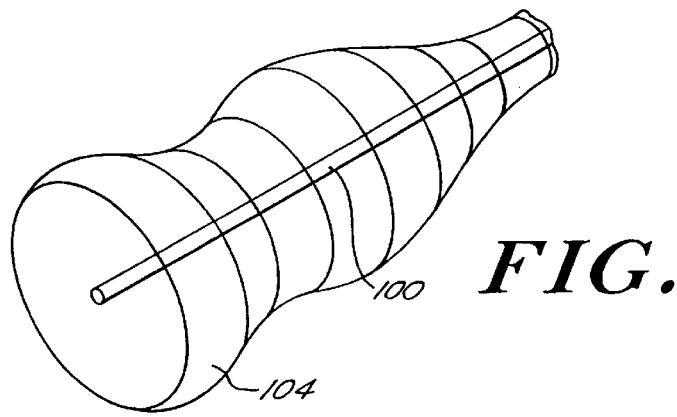
Figure 20A:
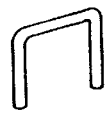
FIGS. 20A–20G are perspective views of various surgical fastening devices made of a transmutable material which is activatable to a radioactive material according to the invention.
Figure 20B:
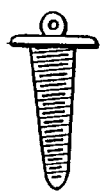
Figure 20D:
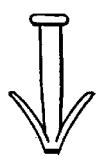
Figure 20C:
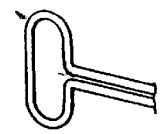
Figure 20E:
Figure 20F:
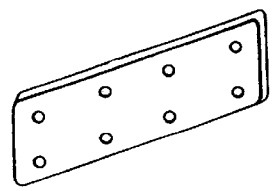
Figure 20G:

Selective masking and/or activation of portions of a device can produce devices which emit radiation in a characteristic pattern which is not solely determined by the shape of the device. For example, a selectively activated rhodium wire 100 may produce a constant-radius radiation pattern 102 along its length, as shown in FIG. 17, or a variable-radius radiation pattern along its length, as shown in FIGS. 18 and 19.

Surgical fastening devices, including, for example, sutures, staples, clips, pins, nails, screws, plates, barbs, anchors, and tissue bridging structures can also be easily fabricated from rhodium and activated to become partially or wholly radioactive as described herein. Such devices are particularly useful in wound repair, in which sections of tissue or bone are joined to promote healing. Patches and other topical application structures are also useful in the administration of therapeutic radiation to a lesion or other localized treatment site that does not necessarily involve or require the joining of tissue for healing purposes. Examples of such devices are illustrated in FIGS. 20A–20G.

The use of accelerated beam technology to transform non-radioactive, transmutable materials to radioactive materials provides several advantages, such as ease of manufacturability of the device and the ability of the device to be reactivated with successive accelerated beam treatments as needed without adversely affecting the structural integrity of the device. The ability to manufacture near-net shape devices from transmutable, non-radioactive materials, and transform them to radioactive devices, in a single fabrication step, is a substantial advantage of the present invention which is not addressed or provided in the prior art.

With the present invention, any desired configuration of the device is obtainable, and any desired radiation is obtainable with the appropriate masking of portions of the device while exposed to the high-energy beam, and/or the appropriate selection of device thickness and beam energy. A significant advantage of fabricating the radiotherapy device from a transmutable material is that fabrication of the device to any desired size, shape or configuration can be done while it is nonradioactive. The device can then be made radioactive in its final form via exposure to a high-energy charged particle beam. The net shape of the device as fabricated will be the net shape of the device in its final, ready-to-use form.

The nuclear transmutation technique for fabricating net-shape and near-net shape radiotherapy devices eliminates many costly process steps and allows the device to be fabricated easily and economically before it is rendered radioactive. In addition, the device can be exposed to an accelerated charged particle beam as many times as is required to effect transmutation of the material of the device. This feature eliminates storage and shelf-life problems associated with prior art radioactive devices. Should the device not be used for treatment during the half-life of the radioactive material, it can simply be reactivated.

Radiotherapy devices according to the present invention are considered to be "sealed source equivalents", as they are suitable for use in applications in which "sealed sources", as defined in the prior art, were required. A significant advantage of employing the transmutation process of the present invention, whereby net or near net shape rhodium targets are activated to form net or near net shape radioactive palladium-103 targets, is the avoidance of the risk of any dissociation of the radioisotope from the native material of the radiotherapy delivery device. Thus, the devices of the present invention are true "sealed source equivalents", as they meet all the safety and handling requirements that are imposed on prior art "sealed source" radiotherapy devices.

The desired transmutation reaction of rhodium to palladium-103 may be accompanied by other undesired transmutation reactions which produce other palladium isotopes that may not be appropriate for radiotherapeutic use, as well as heat. This combination of desired and undesired, or less desirable, reactions may depend not only on the thickness of the radiotherapy delivery structure in the direction of beam penetration, but also at least in part on the energy of the charged particle beam as it penetrates the radiotherapy delivery structure.

Figure 21:
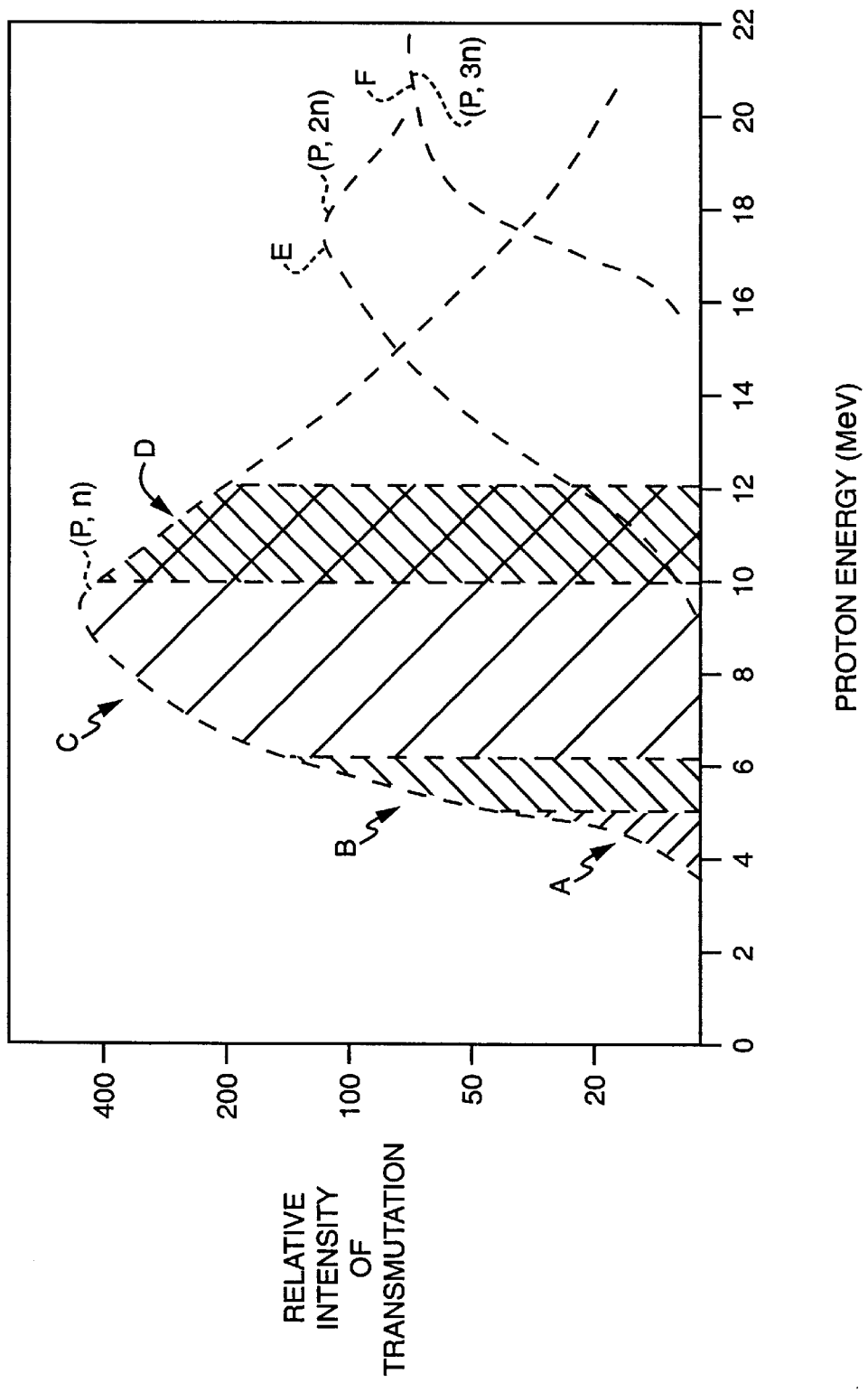
FIG. 21 is an illustrative graph which represents in a general way the relative intensity of various transmutation reactions of rhodium to palladium as a function of the energy of the proton beam.

FIG. 21 is a representative graph which generally illustrates the relative intensity of various transmutation reactions of rhodium-103 to isotopes of palladium as a function of proton energy. The largest peak on the graph illustrates generally an intensity curve for the reaction Rh-103→(p,n)→Pd-103, in which a single proton replaces a single neutron in the nucleus of a rhodium atom. The hatched area A between approximately 4 and 5 MeV indicates an approximate coulomb energy threshold, below which the protons are not sufficiently energized to cause any transmutation reaction. The hatched area B between the coulomb threshold and approximately 6 MeV represents a proton energy level which is still too low to cause any significant transmutation reaction, yet sufficient to produce heat in the rhodium target. The heat must be dissipated in some way so as not to distort or permanently affect the target structure.

At proton energies above approximately 6 MeV, indicated generally by the wide-hatched region C of the graph, the proton energy is sufficient to transmute rhodium to palladium-103. The optimum energy range for efficient transmutation of rhodium to palladium-103 is generally between about 10 and 12 MeV, indicated by the cross-hatched region D of the graph. This amount may vary as a function of the distance of beam penetration into a particular rhodium radiotherapy delivery structure; therefore, the geometry of the structure, and in particular its thickness in the direction of beam penetration, is an important element in determining the likelihood that a desired transmutation reaction will occur.

As indicated generally by the curve E in the graph of FIG. 21, at proton energies greater than about 12 MeV, a second transmutation reaction, Rh-103→(p,2n)→Pd-102, in which a single proton replaces two neutrons in the nucleus of a rhodium atom, becomes more probable. This reaction produces palladium-102, a stable palladium isotope which is not useful for radiotherapy applications.

As indicated by the curve F in the graph, at proton energies greater than about 16 MeV, a third transmutation reaction, Rh-103→(p,3n)→Pd-101, in which a single proton causes the emission of three neutrons from the nucleus of a rhodium atom. This reaction produces radioactive palladium-101, which has a relatively complex decay scheme that is not suitable for radiotherapeutic use and is considered a radioimpurity of palladium-103.

It is desirable to maximize the probability of the desired rhodium-to-palladium-103 transmutation reaction so that the radiotherapy delivery structures can be fabricated to a net or a near-net shape and transmutated without excessive heat generation and without the production of undesirable isotopes and radioisotopes. Power, or heat, is the product of beam energy and beam current. The heat produced in the target in an activating high-energy beam is independent of the extent of transmutation; therefore, heat will be generated in the target as a result of beam activation, regardless of whether any transmutation reactions occur.

One way to manage and prevent excessive heat buildup in the device is to design the radiotherapy delivery structure so that it is sufficiently thick in the direction of beam penetration to absorb energy in the range at which the desired transmutation reaction is most likely to occur. Energy of the beam outside of this range is manifested principally as heat. The device can be dimensioned so that at least a portion of the energy which is primarily heat-producing can pass through the device, or at least be diverted from the radiotherapy delivery structure through a number of possible means, detailed more fully below.

Figure 22:
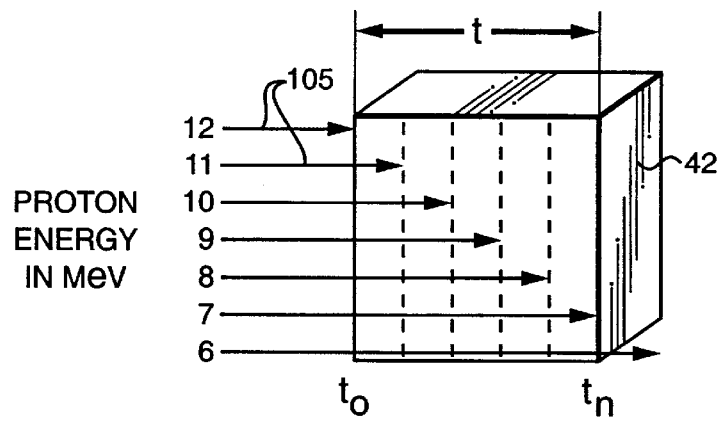
FIG. 22 is a simplified diagram of the penetration of a high-energy proton beam into a rhodium target of thickness t.

The transmutation of the radiotherapy delivery structure, and the heat production within the structure, are each a function of the initial energy of the beam entering the structure and the thickness of the structure in the direction of beam penetration. As shown in FIG. 22, a target formed from rhodium into a net or near net shape radiotherapy delivery structure 42 has a thickness t in the direction of beam penetration. The structure 42 is penetrated by a high-energy proton beam 105. The angle of incidence of the beam is selected to provide an effective amount of the radioisotope throughout the exposed portion of the target and may vary accordingly. As the beam passes through the target, the target absorbs some of the energy from the protons in the beam. The proton energy is attenuated from a nominal level entering the target as a function of the depth of beam penetration, t. The energy spectrum of the protons is preferably selected so that the desired transmutation reaction occurs in the target between its surface, $t_0$, and its ultimate thickness in the direction of beam penetration, $t_n$. The ultimate thickness of the structure is selected so that at least a portion of the energy at which the desired transmutation reaction is most likely to occur is absorbed within the target structure, i.e., between $t_0$ and $t_n$. At an incremental depth $t_{n+1}$ beyond $t_n$, the energy of the beam will be depleted such that it is insufficient for the desired transmutation reaction to occur. Because heating will occur at beam energies greater than 4 MeV, it is preferred to have the device only thick enough to absorb energy that will effect the desired transmutation reaction. At least a portion of the energy which is insufficient to effect the desired transmutation reaction can pass through the device or otherwise be diverted into a heat dissipating medium.

The beam may have an initial energy in excess of that required to effect the desired transmutation reaction, as previously discussed in connection with the graph of FIG. 21. The energy of the beam is therefore preferably selected so as not to effect undesired transmutation reactions in the device which may require greater proton energies than that required for the desired transmutation reaction. Alternatively, the beam energy, if excessive, can be attenuated by an attenuating medium, such as a substantially non-activatable metal, prior to penetration of the transmutable material of the target structure so as to ensure that the charged particles reach the target structure at an energy which is suitable for effecting the desired transmutation reaction.

For the Rh-103→(p,n)→Pd-103 reaction, a proton beam attenuation of approximately 3 MeV can be expected for every 100 micrometers in target thickness. Thus, if a proton beam having a nominal energy of 12 MeV is directed at a rhodium target, the rhodium atoms bombarded by protons at 12 MeV (for example, at $t_0$) will likely be transmutated to palladium-103. Similarly, the rhodium atoms further inside the target (for example, at $t_1$) will be bombarded by protons at 11 MeV and will likely be transmutated to palladium-103, and so on, until at some thickness $t_n$ the proton energy has been attenuated to a level which is insufficient to effect the desired transmutation reaction. At this energy level the proton beam is preferably no longer passing into or through the radiotherapy delivery structure.

Figure 23:
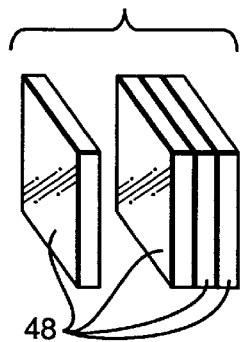
FIG. 23 is a simplified perspective view of a target in the form of a sheet or foil, and several of such delivery structures arranged in a stack to obtain a target having a desired thickness in the direction of beam penetration.

Once the desired thickness of the target radiotherapy delivery structure is known for a given energy level of the activating beam, the desired thickness can be achieved in a variety of ways, such as by stacking or layering a plurality of sheets or foils 48 of a nominal thickness until the desired thickness is obtained, as shown in FIG. 23. Alternatively, the desired thickness can be achieved by angling the structure relative to the activating beam so that the beam impinges on the structure at an oblique angle, and therefore the effective thickness of the structure in the direction of beam penetration is increased or decreased as desired.

Figure 24:
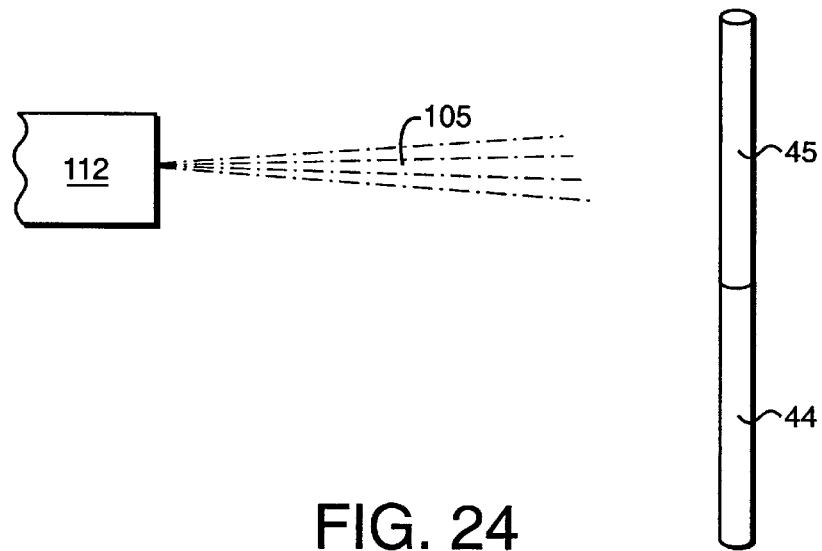
FIG. 24 is a simplified side view of a high-energy beam of protons exiting from a linear accelerator and directed toward a target in the form of a wire having a rhodium tip which is transmutable by the high energy proton beam to radioactive palladium-103.
Figure 25:
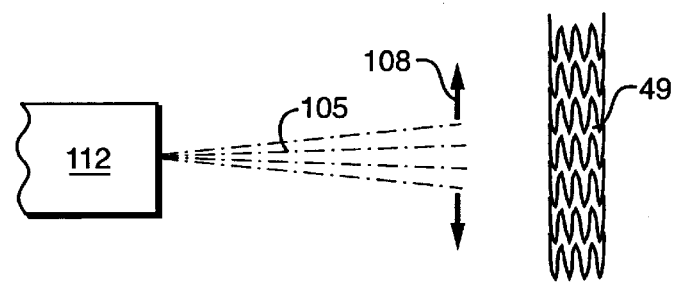
FIG. 25 is a simplified side view of a high-energy beam of protons exiting from a linear accelerator and directed towards a stent made of rhodium wire.

The target radiotherapy delivery structure may be, for example, a microwire 44, as shown in FIG. 24, or a stent 49, as shown in FIG. 25. The structure may be made of rhodium and fully activated. Alternatively, it may be made of a substantially non-activatable material and can include a tip 45, shown in FIG. 24 on the end of guidewire 44, which is made of rhodium and which may be integral with the microwire or otherwise joined with the microwire, such as by a bonding process. The activating beam can be focused on a specific region of the target structure so as to activate only that region. The tip 45 may be of any shape suitable for the application, such as, for example, a coil that fits over an end of the guidewire 44.

It is also possible to increase the effective thickness of a microwire target by coiling it or otherwise shaping it to have greater material thickness in the direction of beam penetration.

Other ways to control heat into and out of the delivery structure involve the control of primarily heat-producing energy into and out of the structure. Of these two modes of thermal management, it is preferable to limit the heat which enters the delivery structure so that removal of excess heat is not necessary. However, if excessive heating of the delivery structure cannot be avoided during proton activation, means for effectively dissipating heat from the structure must also be employed.

As previously mentioned, the radiotherapy delivery structure can be designed so that its thickness in the direction of beam penetration is sufficient to ensure that at least a portion of the energy which effects the desired transmutation reaction is absorbed into the structure, while at least a portion of the energy below the threshold for the desired transmutation reaction passes out of the structure or is otherwise diverted to a heat exchange medium. The structure thus can act as an energy "filter" which preferentially absorbs energy of at least about 6 MeV, and up to about 16 MeV, and does not absorb significant energy outside of this approximate range.

Figure 26:
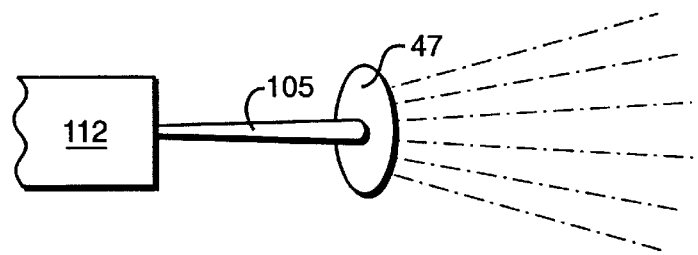
FIG. 26 is a simplified side view of a high-energy beam of protons exiting from a linear accelerator and passing through a beam diffuser before impinging on a target.

Another way to minimize heat input to the delivery structure is to reduce the power density on the target structure from the beam. One way to do this is to create a relatively broad, uniform beam spot on the target structure, such as by diffusing the beam through a diffuser or other beam attenuating element 47, as shown in FIG. 26, or by directing the beam over a relatively long distance so that it diverges naturally into a relatively large beam spot. Another way to accomplish this is to scan the beam over the surface of one or more target structures, as shown by arrows 108 in FIG. 25. Alternatively, one or more target structures can be moved into and out of the beam, which is directed over a relatively large area.

Figures 27, 28:
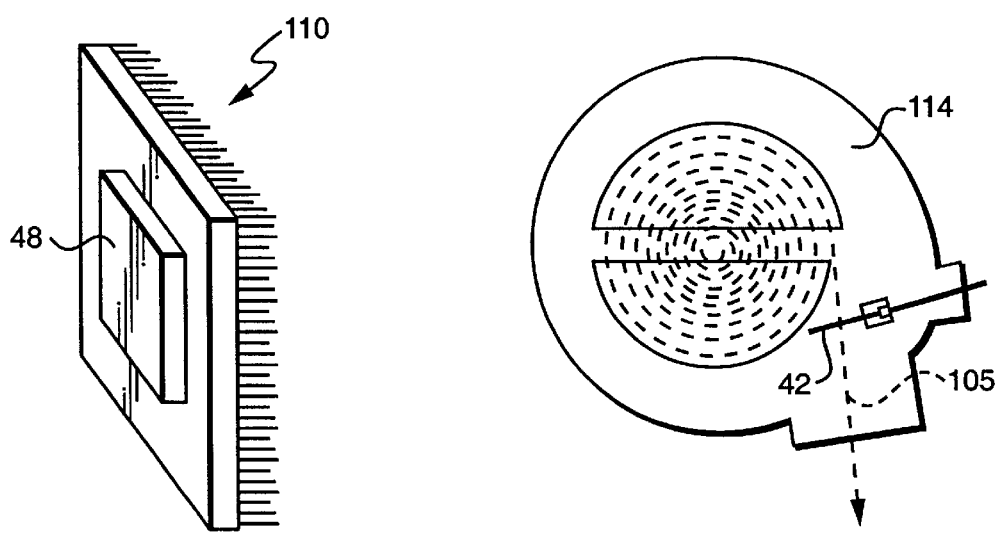
FIG. 27 is a perspective view of a rhodium target in the form of a foil or sheet mounted on a finned, non-activatable heat dissipating member.
FIG. 28 is a simplified plan view of a cyclotron, in which a high-energy beam of protons is accelerated toward a rhodium target.

Heat produced in the target structure can be dissipated, for example, by placing a thermally conductive heatsink member 110 in thermal communication with the target. The heatsink member 110 is preferably any substantially non-activatable metal or ceramic. For example, as shown in FIG. 27, the target, shown as a foil 48, can be removably mounted to a thermally conductive plate 110 with fins or other heat dissipating members, as shown in FIG. 27. Cooling of the plate can be accomplished with gas, liquid or other suitable thermally conductive media. For conductive cooling, it is preferred to make maximum thermal contact between the target and the heatsink member to maximize heat transfer from the target. This can be done with the use of mechanical bonding agents, including conductive coatings, as well as by applying a mechanical force between the target and the heatsink member to increase the extent of contact between them, such as, for example, by wrapping a wire from the target around a thermally conductive spool, drum, sheet or the like.

The high-energy beam is preferably obtained from a linear accelerator or a cyclotron 114, shown in FIG. 28. The beam preferably is directed to the rhodium target at an incident angle which is selected as a function of the energy of the beam and the thickness of the radiotherapy delivery structure. It is desirable to select these parameters so that at least a substantial portion of the energy below the coulomb barrier is dissipated in the underlying heat dissipating system and not in the radiotherapy delivery structure.

Figure 29:
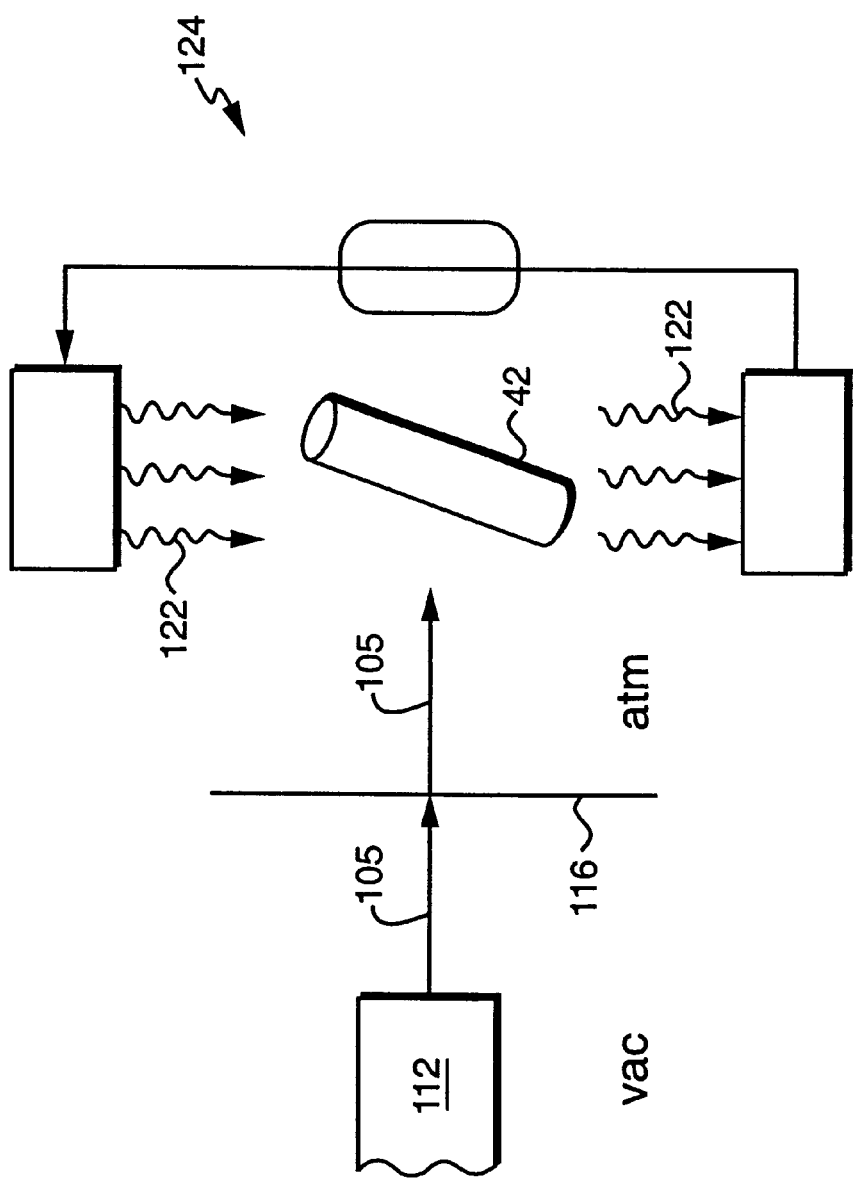
FIG. 29 is a simplified schematic diagram of a cooling mechanism for the radiotherapy delivery structure.

The thermally conductive heat transfer approach may not be feasible if the target structure remains within the evacuated chamber associated with the cyclotron or linear accelerator. This is because in a vacuum, conductive and convective cooling are relatively ineffective. Thus, as an alternative, the target structure can be cooled by a highly efficient, chemically inert heat transfer fluid, such as, for example, helium. As shown in FIG. 29, this can be accomplished by including a seal 116 between the cyclotron or linear accelerator, which is at vacuum, and the end station where the target structure 42 is located, which may be at atmospheric pressure. The seal 116 is preferably a thin metal window having a relatively high heat capacity, a low charged number, and good cooling properties. Beryllium and aluminum are preferred metals which can effectively provide an atmospheric seal between the cyclotron and the end station. The high energy proton beam 105 will pass through the window and impinge on the target structure, which is preferably located close to the window to minimize energy dissipation in the heat conductive medium. A cooling fluid 122, such as helium, can be passed over the target structure to transfer heat from the target structure to a heat exchanger, illustrated schematically at 124.

Heat can also be diverted from the target structure via radiative heat transfer. For optimum radiative heat transfer, it is preferable to maximize the temperature differential between, and/or the thermal emissivities of, the target and the heat transfer medium surrounding it.

Although a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An implantable interstitial radiotherapy device for in situ delivery of radiation to tumorous tissue, comprising:

a net or near net shape interstitial radiotherapy delivery structure made substantially of rhodium, wherein a portion of the rhodium is transformed into palladium-103 upon activation by a beam of charged particles including protons having energy above a predetermined threshold energy, at least a portion of the energy in excess of the predetermined threshold energy being captured within the radiotherapy delivery structure and used to form the palladium-103 and at least a portion of the energy below the predetermined threshold energy not being retained in the radiotherapy delivery structure, wherein the protons have an energy of at least approximately 4 MeV, wherein the predetermined threshold energy of the charged particles is at least approximately 6 MeV, and wherein transformation of the radiotherapy delivery structure, and heat production within the structure, are functions of initial energy of the beam of charged particles entering the structure and thickness of the structure in the direction of beam penetration.

2. A radiotherapy device according to claim 1, wherein the radiotherapy delivery structure is a wire and is formed either to a desired net shape prior to activation, or to a desired near-net shape prior to activation and to a desired net shape after activation.

3. A radiotherapy device according to claim 1, wherein the radiotherapy delivery structure is a substantially three-dimensional shape.

4. A radiotherapy device according to claim 1, wherein the device is selected from the group consisting of sutures, staples, clips, pins, nails, wires, screws, barbs, anchors, plates and plaques.

5. A radiotherapy device according to claim 1, wherein the radiotherapy delivery structure is a coiled wire.

* * * * *